United States Patent
Grossman et al.

(10) Patent No.: US 6,655,190 B2
(45) Date of Patent: Dec. 2, 2003

(54) FIXED BEAM HIGH-G SHOCK PULSE GENERATOR APPARATUS AND METHOD

(75) Inventors: Owen D. Grossman, Golden Valley, MN (US); Mark W. Weber, Zimmerman, MN (US); Jeffrey E. Fridberg, Anoka, MN (US)

(73) Assignee: Honeywell International Inc., Morristown, NJ (US)

( * ) Notice: Subject to any disclaimer, the term of this patent is extended or adjusted under 35 U.S.C. 154(b) by 194 days.

(21) Appl. No.: 09/998,700

(22) Filed: Nov. 30, 2001

(65) Prior Publication Data

US 2003/0101794 A1 Jun. 5, 2003

(51) Int. Cl.$^7$ ................................................. G01N 3/08
(52) U.S. Cl. ..................................................... 73/12.07
(58) Field of Search ............................. 73/11.04, 12.01, 73/12.04, 12.06, 12.07, 12.08, 12.09

(56) References Cited

U.S. PATENT DOCUMENTS 4,884,456 A * 12/1989 Meline et al. ................. 73/826
5,487,298 A * 1/1996 Davis et al. ................. 73/12.05

OTHER PUBLICATIONS

Author: Danelle M. Tanner, Jeremy A. Walraven, Karen Helgesen, Lloyd W. Irwin, Fredrick Brown, Norman F. Smith, Nathan Masters, Title: "MEMS Reliability In Shock Environments", presented at IEEE International Reliability Physics Symposium, San Jose, CA, Apr. 10–13, 2000, pp. 129–138.

Author: Vesta I. Bateman, Fred A. Brown, Neil T. Davie, Title "The Use Of A Beryllium Hopkinson Bar To Characterizr A Piezoresistive Accelerometer In Shock Environments", presented in the 1996 Proceedings Of The Institute of Environmental Sciences, pp 336–343.

Author: Cyril M. Harris, Charles E. Crede, Title: "Shock And Vibration Handbook", Second Edition, McGraw–Hill Book Company, pp 25–24 and 25–25.

* cited by examiner

Primary Examiner—Max Noori
(74) Attorney, Agent, or Firm—Matthew S. Luxton

(57) ABSTRACT

An apparatus and method for use in testing devices under high-g environments is disclosed in which an elastic beam, rigidly fastened at least at one end, carries the device under test; the beam being pre-loaded to a bent position by a force producing member which may be suddenly removed to allow the stored energy of the beam to be released, and to apply a high-g force to the device.

20 Claims, 1 Drawing Sheet

US 6,655,190 B2

FIXED BEAM HIGH-G SHOCK PULSE GENERATOR APPARATUS AND METHOD

BACKGROUND OF THE INVENTION

1. Field of the Invention

The present invention relates to the field of shock testing and more particularly to an apparatus and method for subjecting a test specimen to a high-g shock in the laboratory to simulate the conditions the specimen might encounter in actual use.

2. Description of the Prior Art

Of course, a test specimen may be tested at a Proving Ground under substantially identical conditions as will be encountered in actual use. However, the cost of transporting the specimen to the Proving Ground is very high and only one or two tests per day can be performed. Accordingly, it is desired that a laboratory test be provided so as to minimize expense and increase convenience, so that several tests per day can be performed.

Laboratory shock testing apparatus, utilizing a device identified as a Hopkinson bar is known in the art. Such apparatus is described in a paper entitled *"The Use of a Beryllium Hopkinson Bar to Characterize a Piezoresistive Accelerometer in Shock Environments"* presented by Vesta I. Bateman, Fred A. Brown, and Neil T. Davis of Sandia National Laboratories in Albuquerque, N. Mex., in the 1996 *Proceedings of the Institute of Environmental Sciences* on pages 336–343. This prior system employs a Hopkinson bar, i.e., a perfectly elastic homogeneous bar of constant cross-section which has first and second end surfaces substantially perpendicular to the length. A test specimen, in this case an accelerometer, is mounted on the surface at the first end and the bar is then impacted on the surface at the second end by a projectile that is fired by an air gun down a long tube to produce a shock wave that travels the length of the bar and applies a high-g force to the specimen. The prior art has several disadvantages, among which is the fact that to produce a sufficiently high-g force, a relatively large projectile traveling at high speed must be used (the higher the force desired, the greater the size and/or speed of the projectile). This requires a significantly long tube (e.g., up to 40 feet) for the projectile to reach the desired speed necessary to produce a high-g force (for example, say above 10,000). Thus, a great deal of laboratory space needs to be provided, which is costly and inconvenient. Furthermore, the greater size and speed of the projectile introduces greater danger in performing the test. Also, the period or duration of the high-g shock varies inversely with the amplitude of the shock (i.e., the higher the g-force desired, the shorter the duration of the shock; usually considerably less than one second).

SUMMARY OF THE INVENTION

The present invention uses step relaxation of a very stiff spring to attain the high-g levels. The spring, a fixed beam which, in a preferred embodiment comprises an I-beam of high strength aluminum, is used to mount the test specimen. The beam is put under high strain, such as by applying a large force, tending to bend the beam to near capacity (i.e., its yield point), and then the stored energy in the beam is released by suddenly removing the force to produce a high-g shock that has a significantly long duration (for example about one second) which is independent of the magnitude of the shock. Furthermore, in the present invention it is simple, inexpensive, and does not require excessive laboratory space.

DETAILED DESCRIPTION OF THE PREFERRED EMBODIMENTS

Figure 1:
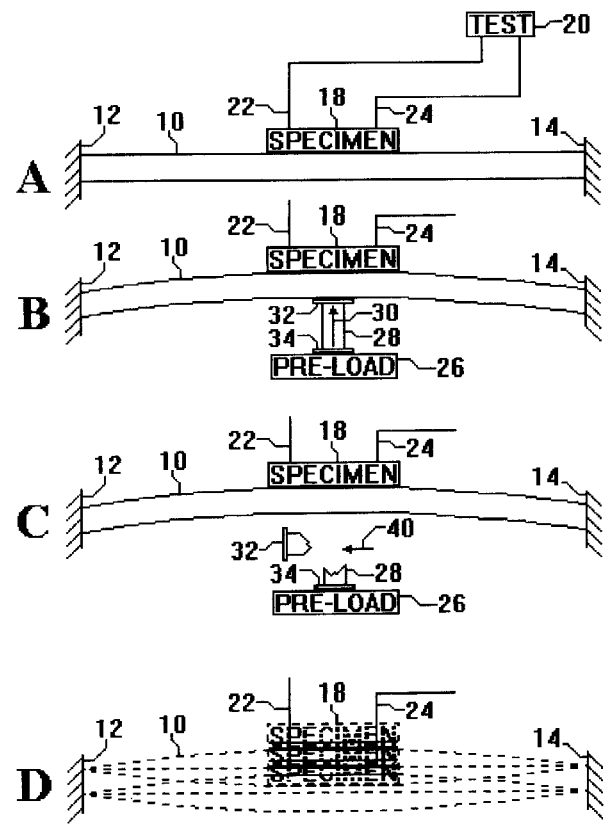
FIG. 1A shows a side view of the beam with a specimen attached.
FIG. 1B shows the beam of FIG. 1A with an applied force bending the beam upwardly.
FIG. 1C shows the beam of FIG. 1B with the applied force suddenly removed.
FIG. 1D shows the beam of FIG. 1C under a high-g shock.

In FIG. 1A, a beam 10 of high strength aluminum, which preferably is shaped in the form of an I-beam, is shown rigidly connected at both ends to a solid structure shown by the cross hatched portions 12 and 14. High strength aluminum has been chosen in the preferred embodiment because of its high yield point (i.e., its ability to flex without permanent deformation), its low cost, and the ease with which it may be machined. Alternately, titanium and other high-yield-point materials may be used but generally at a higher cost. An I-beam configuration is used to provide strength and store energy with as little weight as possible. In general, the greater the weight, the less amplitude of energy stored.

In FIG. 1A, a specimen 18 to be tested, which may be any of a variety of devices such as a printed circuit, an accelerometer, or a gyroscope, is fastened to the middle of the beam 10 for purposes to be explained below. The specimen 18 is connected to test apparatus 20 by connectors such as wires 22 and 24 to record or monitor the effects of the high-g test.

In FIG. 1B, the apparatus of FIG. 1A is repeated with the same reference numerals and, in addition, a force, or pre-load producing device 26 which may be a hydraulic ram, is shown connected by a member 28 to produce an upwardly directed force shown by an arrow 30. Member 28 is preferably a frangible material with high compression strength, such as a ceramic, to allow sudden fracture. In the preferred embodiment, member 28 is provided with protective ends 32 and 34 to apply the force over a larger area, to help prevent the formation of indentations in the aluminum beam 10. The beam 10 is bent upwardly by an amount depending on the g-force required, but in no event past the yield point.

In FIG. 1C, the apparatus shown in FIG. 1B is repeated with the same reference numerals but, in FIG. 1C, a projectile or other shattering device shown by an arrow 40 is depicted as breaking or shattering the member 28 so that beam 10 is suddenly allowed to spring back downwardly, producing a high-g shock wave applied to the specimen 18.

This action is depicted in FIG. 1D where the specimen is shown moving down and up until it is quickly damped to a standstill, as in FIG. 1A. The high-g force, the maximum of which occurs during the first full cycle, is in the form of a damped sinusoid. If it was desirable to change the damping characteristics of the system, some damping member, such as a dash pot, might be attached to the beam 10. The projectile or shattering device may be relatively small, and may be propelled by a pneumatic device and a relatively short coiled tube (not shown). Since the projectile does not impart the shock wave to the bar, its size and speed need only be great enough to shatter the ceramic. This minimizes the danger and space requirements of the prior art. The application of a high-g force requires a relatively sudden release of beam 10, and the magnitude of the force may be adjusted using different amounts of bending for various requirements dictated by the specimen 18. The specimen 18 is shown attached near the center of beam 10 so that the g-force is directed primarily upwardly, and secondary g-forces in other directions are minimized. This is especially desirable for testing inertial devices.

Figure 2:
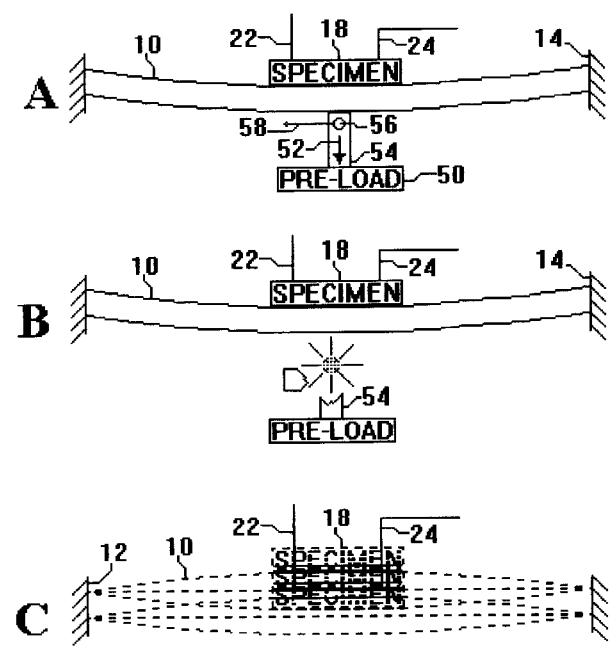
FIG. 2A shows an alternate arrangement of the beam of FIG. 1 with an applied force bending the beam downwardly.
FIG. 2B shows the beam of FIG. 2A with the applied force suddenly removed.
FIG. 2C shows the beam of FIG. 2B under a high-g shock.

FIGS. 2A–C show an alternative embodiment where the force applied to the beam is downwardly, rather than upwardly. FIG. 2A shows the same structure with the same reference numerals as in FIG. 11B except that a pre-load device 50, which again may be a hydraulic ram positioned to operate in the opposite direction, is shown pulling beam 10 downwardly, as shown by arrow 52 through a member 54. Since ceramic does not have good tensile strength, a material such as steel may be used, and a separation device such as a sheared cable or, preferably, an explosive bolt 56 detonated by an electric signal through wire 58, may be used to cause the sudden disconnect of member 54.

In FIG. 2B, the explosive bolt 56 of FIG. 2A has been activated, which suddenly separates member 54 to allow beam 10 to move upwardly and apply the high-g force to the specimen. Although an explosive bolt 56 is shown, other sudden separation devices that can cause the rupture of the member 54 may also be used.

FIG. 2C is the same as FIG. 1D and shows the beam 10 and specimen 18 moving up and down until brought to a standstill by the damping.

While in the preferred embodiments the beam 10 has been shown rigidly connected at both ends, in some cases connecting the beam 10 at only one end, in cantilever fashion, could be used. In such a case, the movement of the beam 10 would have an angular component that could be tolerated for testing devices that do not require purely linear motion as do most inertial devices.

In a preferred embodiment, the beam 10 is about 12 inches long and about ¾ inches wide. The yield point is such that bending the beam by about ⅛ inch produces no permanent deformation, and g-forces up to about 17,000 have been produced. Of course, lesser g-forces can be attained by bending the beam less than ⅛ inch and by using different dimensions and different materials. It is also possible to produce forces in excess of 17,000 g with proper choice of materials, dimensions, and bending.

It is therefore seen that we have provided a simple, inexpensive, and space saving testing device which produces a desired high-g shock force with smaller, less dangerous equipment, that does not depend on a large, high speed projectile to provide the shock. Furthermore, our invention provides a greater duration of shock and is able to vary the amount of g-force produced with a simple bending adjustment that was not available in the prior art.

Many changes or modification to the invention described herein will occur to those skilled in the art. As mentioned, different materials and different methods of applying the bending force may be substituted, as well as devising different ways of causing the sudden release of the energy in the beam. Accordingly, we do not intend to be limited to the specific structures used to describe the preferred embodiments. The scope of the invention may be determined in accordance with a reasonable interpretation of the appended claims.

What is claimed is:

1. A high-g shock-producing device for testing a sample specimen comprising:
   a beam of predetermined length having at least one end substantially rigidly fixed with the specimen mounted thereon at a position remote from the one end;
   a device positioned to apply a force causing the beam to bend in a direction transverse to the length; and
   means for suddenly removing the force so as to release the beam and produce a high-g shock on the specimen.

2. The apparatus according to claim 1, wherein the beam is rigidly fixed at both ends.

3. The apparatus according to claim 2, wherein the specimen is attached at approximately the middle of the beam.

4. The apparatus according to claim 3, wherein the device comprises an upwardly directed pushing member connected proximate the center of the beam.

5. The apparatus according to claim 3, wherein the device includes a hydraulic ram.

6. The apparatus according to claim 5, wherein the device further includes a frangible member between the hydraulic ram and the beam.

7. The apparatus according to claim 6, further including a breaking member to rupture the frangible member, to suddenly remove the force applied to the beam.

8. The apparatus according to claim 7, wherein the frangible member comprises a ceramic and the breaking member comprises a projectile.

9. The apparatus according to claim 3, wherein the device comprises a downwardly directed pulling device connected proximate the center of the beam.

10. Apparatus according to claim 9, further including a breakable device between the downwardly directed pulling device and the beam.

11. The apparatus according to claim 10, further including a breaking member to rupture the breakable device, to suddenly remove the force applied to the beam.

12. The apparatus according to claim 11, wherein the breaking member is an explosive bolt.

13. The apparatus according to claim 1, wherein the beam comprises high strength aluminum.

14. The apparatus according to claim 1, wherein the beam is configured as an I-beam.

15. The method of producing a high-g force on a test device comprising the steps of:
   A) mounting a beam rigidly at least at one end;
   B) mounting the device on the beam at a position remote from the one end;
   C) applying a force to the beam in a direction to bend the beam by a predetermined amount; and
   D) suddenly removing the force to release the beam, to produce a high-g force on the device.

16. The method of claim 15, wherein step A includes supporting the beam rigidly at both ends thereof.

17. The method of claim 16, wherein the position of step B is substantially the middle of the beam.

18. The method of claim 17, wherein step C includes a frangible device.

19. The method of claim 18, wherein step D includes breaking the frangible device.

20. A high-g shock producing device for testing a specimen comprising:

an I-beam of high strength aluminum mounted rigidly at both ends;

means for mounting the specimen atop the I-beam proximate the center thereof;

a ceramic member positioned to bear against the bottom of the I-beam proximate the center;

a hydraulic ram positioned to produce an upwardly directed force on the ceramic member to cause the I-beam to bend to a position below the yield point thereof;

a projectile shooting device positioned to direct a projectile at the ceramic member to cause it to fracture and remove the upwardly directed force thereby allowing the I-beam to suddenly un-bend and apply a high-g force to the specimen.

* * * * *